United States Patent
Harris et al.

(10) Patent No.: US 12,295,547 B2
(45) Date of Patent: May 13, 2025

(54) PORTABLE MEDICAL DEVICES, SYSTEMS, AND METHODS OF OPERATION

(71) Applicant: GLOBALMEDIA GROUP, LLC, Scottsdale, AZ (US)

(72) Inventors: Michael D. Harris, Scottsdale, AZ (US); Joel E. Barthelemy, Ft Lauderdale, FL (US)

(73) Assignee: GLOBALMED HOLDINGS, LLC, Scottsdale, AZ (US)

( * ) Notice: Subject to any disclaimer, the term of this patent is extended or adjusted under 35 U.S.C. 154(b) by 0 days.

(21) Appl. No.: 18/117,340

(22) Filed: Mar. 3, 2023

(65) Prior Publication Data
US 2024/0293001 A1  Sep. 5, 2024

(51) Int. Cl.
| A61B 1/00 | (2006.01) |
| A61B 1/04 | (2006.01) |
| A61B 1/045 | (2006.01) |
| A61B 1/05 | (2006.01) |
| A61B 1/227 | (2006.01) |
| A61B 1/24 | (2006.01) |
| A61B 1/247 | (2006.01) |

(52) U.S. Cl.
CPC ...... *A61B 1/00016* (2013.01); *A61B 1/00188* (2013.01); *A61B 1/045* (2013.01); *A61B 1/046* (2022.02); *A61B 1/05* (2013.01); *A61B 1/227* (2013.01); *A61B 1/24* (2013.01); *A61B 1/247* (2013.01)

(58) Field of Classification Search
CPC . A61B 1/00016; A61B 1/046; A61B 1/00188; A61B 1/045; A61B 1/05; A61B 1/227; A61B 1/24; A61B 1/247
USPC .......................................................... 348/77
See application file for complete search history.

(56) References Cited

U.S. PATENT DOCUMENTS

| 5,638,302 A * | 6/1997 | Gerber ................ B60R 13/10 194/902 |
| 10,799,088 B2 * | 10/2020 | Kashima ............ A61B 1/00043 |
| 2005/0043583 A1 * | 2/2005 | Killmann ............... A61B 1/041 600/109 |
| 2010/0012417 A1 * | 1/2010 | Walter ................ B60K 28/063 455/556.1 |
| 2010/0305409 A1 * | 12/2010 | Chang ..................... A61B 1/05 600/240 |

(Continued)

FOREIGN PATENT DOCUMENTS

GB        159690       3/1921

OTHER PUBLICATIONS

ISA; PCT International Search Report and the Written Opinion dated Jul. 11, 2024 in Application PCT/US24/14592.
(Continued)

*Primary Examiner* — Matthew David Kim
(74) *Attorney, Agent, or Firm* — SNELL & WILMER L.L.P.

(57) ABSTRACT

A telemedicine system can include a telemedicine management system configured to be wirelessly coupled to a portable medical device. The portable medical device can include at least one camera operably coupled to a main body. The portable medical device can be configured to transmit video data from the at least one camera to the telemedicine management system. The telemedicine management system can be configured to share the video data through a videoconference.

18 Claims, 9 Drawing Sheets

(56) References Cited

U.S. PATENT DOCUMENTS

| | | | | |
|---|---|---|---|---|
| 2013/0057828 | A1* | 3/2013 | de Smet | A61B 3/12 |
| | | | | 351/207 |
| 2013/0211265 | A1* | 8/2013 | Bedingham | A61B 5/002 |
| | | | | 600/300 |
| 2020/0409549 | A1* | 12/2020 | Yang | H04N 23/80 |
| 2021/0113056 | A1* | 4/2021 | Levy | G02B 23/2423 |
| 2021/0298566 | A1* | 9/2021 | Levy | A61B 1/00105 |
| 2022/0170795 | A1* | 6/2022 | Bruno | G01J 5/12 |
| 2022/0331047 | A1* | 10/2022 | Shelton, IV | G16H 20/40 |
| 2023/0099863 | A1* | 3/2023 | Pesach | G06V 40/165 |
| | | | | 382/103 |
| 2023/0248239 | A1* | 8/2023 | Mersinger | A61B 5/022 |
| | | | | 600/301 |
| 2024/0000397 | A1* | 1/2024 | Merigian | A61B 5/01 |

OTHER PUBLICATIONS

'GlobalMed Telemedicine—Pediatric Consult' (GlobalMed Virtual Health Solutions) Apr. 13, 2016 (Apr. 13, 2016); retrieved from internet Sep. 17, 2024: URL=<https://www.youtube.com/watch?v=4xOJOm393eU ( Cite No. 00400).

'GlobalMedia TotalExam Cam for Telemedicine (GlobalMed Virtual Health Solutions)' Jun. 10, 2009 (Jun. 10, 2009); retrieved from internet Sep. 17, 2024; URL=<https://www.youtube.com/watch?v=3yZ1wz26qGM:( Cite No. 00500).

* cited by examiner

SECT Z-Z'

PORTABLE MEDICAL DEVICES, SYSTEMS, AND METHODS OF OPERATION

FIELD

The present disclosure generally relates to telemedicine devices, systems, and methods, and more particularly to portable medical devices systems, and methods of operation.

BACKGROUND

Telemedicine, or telehealth, allows a health care provider care for a patient without an in-person office visit. Telemedicine is primarily performed online with access on a computer, tablet or smartphone. For example, telemedicine can include a phone call, a video chat, texting between patients and doctors, and/or remote monitoring (i.e., a patient taking his or her temperature and/or blood pressure) and providing the measurements to a doctor.

Virtual visits are growing in popularity. Telehealth can provide various benefits, such as reduced exposure of sick patients to the public, reduced travel time for patients, shorter wait times for appointments, and/or increased access to specialist that are located far away from a patient's residence. Accordingly, portable medical devices, systems, and methods of operation that facilitate telemedicine may be desirable.

SUMMARY

Disclosed herein is a portable medical device that is configured for home use and/or use in emergency situations, such as on an airplane, on a ship, or the like. In various embodiments, the portable medical device can facilitate an in-home checkup exam of a patient, without the patient having to visit a respective doctors office. In various embodiments, the portable medical device includes a first camera configured to facilitate examination of an ear of a patient, and a second camera configured to facilitate examination of a throat and/or nose of a patient. In various embodiments, the portable medical device is configured to take a temperature of a patient. In various embodiments, the portable medical devices is configured to transmit data recorded from the portable medical device to a doctor through a telemedicine management system. In various embodiments, the patient can communicate with a respective doctor through the telemedicine management system during a telehealth visit.

A portable medical device is disclosed herein. In various embodiments, the portable medical device comprises a main body extending from a first end to a second end; a first camera disposed at the first end; and a second camera disposed at the second end.

In various embodiments, the main body defines a longitudinal axis, the first camera defines a first optical axis, the second camera defines a second optical axis, and the first optical axis and the second optical axis are substantially parallel to the longitudinal axis. In various embodiments, the first optical axis and the second optical axis are co-axial.

In various embodiments, the main body defines a grip.

In various embodiments, the first camera includes a video scope configured for adjustable magnification of an object. In various embodiments, the second camera comprises a lens having a fixed magnification.

In various embodiments, the portable medical device further comprises a first button electrically coupled to the first camera, the first button configured to freeze a first frame of the first camera in response to being depressed. In various embodiments, the portable medical device further comprises a second button electrically coupled to the second camera, the second button configured to freeze a second frame of the second camera in response to being depressed.

In various embodiments, the portable medical device further comprises a plurality of lights disposed circumferentially around the first camera.

In various embodiments, the portable medical device further comprises a tongue depressor configured to be coupled to the main body.

In various embodiments, the portable medical device further comprises an extended mirror coupled to the main body.

An electronic system for a portable medical device is disclosed herein. In various embodiments, the electronic system, comprises a transistor circuit comprising a first power rail and a second power rail, the transistor circuit configured to determine a body temperature of a user; a first image sensor; a second image sensor; an infrared sensor on each image sensor side; a transmitter; and a controller in electronic communication with the first image sensor, the second image sensor, the infrared sensor, and the transmitter, the controller configured to command the transmitter to transmit the data to a user device.

In various embodiments, the controller is configured to transmit a first video data from the first image sensor, a second video data from the second image sensor, and infrared data from the infrared sensor.

In various embodiments, the electronic system further comprises a shared frame buffer and pass through disposed electrically between the controller and the first image sensor, between the controller and the second image sensor, and between the controller and the infrared sensor.

In various embodiments, the electronic system further comprises a radio module including the transmitter and a WiFi module including a second transmitter, wherein the radio module is configured to transmit the data to the user device directly, and wherein the WiFi module is configured to transmit the data to the user device through a network.

A portable medical kit is disclosed herein. In various embodiments, the portable medical kit comprises: a portable medical device including a main body, a first camera, and a first control button, the main body extending from a first end to a second end, the first camera disposed at the first end, the first control button configured to control a parameter of the first camera; an extended mirror configured to detachably couple to the main body; and a tongue depressor configured to detachably couple to the main body.

In various embodiments, the portable medical device further comprises a second camera disposed at the second end.

In various embodiments, the first camera defines a first optical axis and the main body defines a longitudinal axis, and wherein the first optical axis and the longitudinal axis are substantially parallel.

In various embodiments, the portable medical device further comprises a plurality of lights at the first end of the main body. In various embodiments, the plurality of lights are configured to illuminate an object within a field of view of the first camera.

BRIEF DESCRIPTION OF THE DRAWINGS

The subject matter of the present disclosure is particularly pointed out and distinctly claimed in the concluding portion of the specification. A more complete understanding of the present disclosure, however, may best be obtained by referring to the following detailed description and claims in connection with the following drawings. While the drawings illustrate various embodiments employing the principles described herein, the drawings do not limit the scope of the claims.

DETAILED DESCRIPTION

The detailed description of various embodiments herein makes reference to the accompanying drawings and pictures, which show various embodiments by way of illustration. While these various embodiments are described in sufficient detail to enable those skilled in the art to practice the disclosure, it should be understood that other embodiments may be realized and that logical and mechanical changes may be made without departing from the spirit and scope of the disclosure. Thus, the detailed description herein is presented for purposes of illustration only and not for purposes of limitation. For example, the steps recited in any of the method or process descriptions may be executed in any order and are not limited to the order presented. Moreover, any of the functions or steps may be outsourced to or performed by one or more third parties. Modifications, additions, or omissions may be made to the systems, apparatuses, and methods described herein without departing from the scope of the disclosure. For example, the components of the systems and apparatuses may be integrated or separated. An individual component may be comprised of two or more smaller components that may provide a similar functionality as the individual component. Moreover, the operations of the systems and apparatuses disclosed herein may be performed by more, fewer, or other components and the methods described may include more, fewer, or other steps. Additionally, steps may be performed in any suitable order. As used in this document, "each" refers to each member of a set or each member of a subset of a set. Furthermore, any reference to singular includes plural embodiments, and any reference to more than one component may include a singular embodiment. Although specific advantages have been enumerated herein, various embodiments may include some, none, or all of the enumerated advantages.

Systems, methods, and computer program products are provided. In the detailed description herein, references to "various embodiments," "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Figure 1:
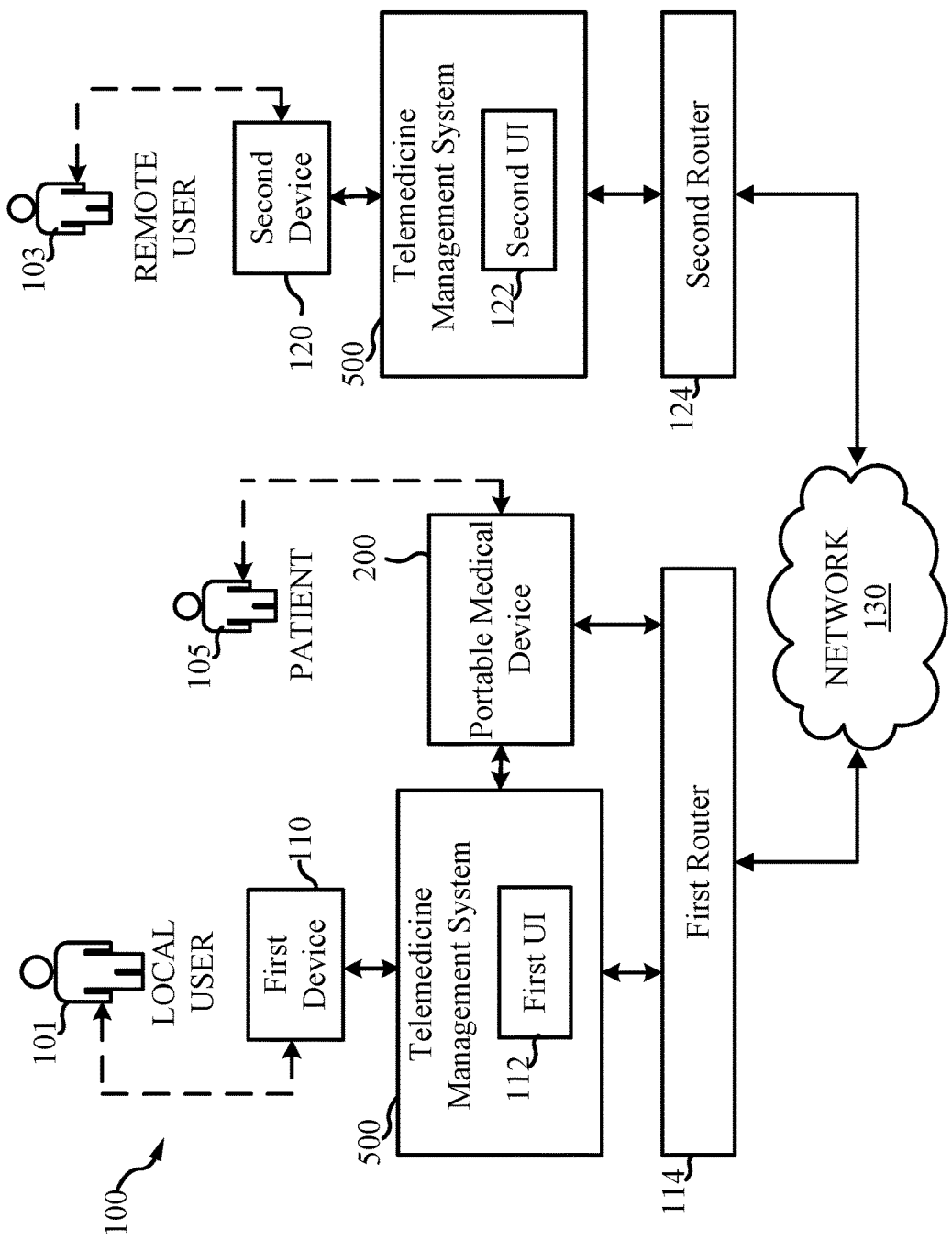
FIG. 1 illustrates a schematic view of a telemedicine system, in accordance with various embodiments.

Referring now to FIG. 1, a schematic view of a telemedicine system 100 for facilitating a remote diagnosis and treatment of a patient 105 with a portable medical device 200, in accordance with various embodiments. In various embodiments, the telemedicine system 100 can be configured to facilitate a home visit (e.g., by a parent, sibling, guardian, the patient, etc.). In various embodiments, the telemedicine system 100 can be configured to facilitate communications with a doctor in an emergency situation (e.g., on an airplane, a boat, or the like). The present disclosure is not limited in this regard.

As shown in FIG. 1, the telemedicine system 100 comprises a telemedicine management system 500. As will be appreciated by one of ordinary skill in the art, the telemedicine management system 500 may be embodied as a customization of an existing system, an add-on product, a processing apparatus executing upgraded software, a stand-alone system, a distributed system, a method, a data processing system, a device for data processing, and/or a computer program product. Accordingly, any portion of the system or a module may take the form of a processing apparatus executing code, an internet-based embodiment, an entirely hardware embodiment, or an embodiment combining aspects of the internet, software, and hardware. Furthermore, the system may take the form of a computer program product on a computer-readable storage medium having computer-readable program code means embodied in the storage medium. Any suitable computer-readable storage medium may be utilized, including hard disks, optical storage devices, magnetic storage devices, and/or the like.

In various embodiments, the telemedicine management system 500 comprises a computer-based system. In various embodiments, components, modules, and/or engines of the telemedicine management system 500 may be implemented as micro-applications or micro-apps. Micro-apps are typically deployed in the context of a mobile operating system, including for example, a WINDOWS® mobile operating system, an ANDROID® operating system, an APPLE® iOS operating system, a BLACKBERRY® company's operating system, and the like. The micro-app may be configured to leverage the resources of the larger operating system and associated hardware via a set of predetermined rules which govern the operations of various operating systems and hardware resources. For example, where a micro-app desires to communicate with a device or network other than the mobile device or mobile operating system, the micro-app may leverage the communication protocol of the operating system and associated device hardware under the predetermined rules of the mobile operating system. Moreover, where the micro-app desires an input from a user, the micro-app may be configured to request a response from the operating system which monitors various hardware components and then communicates a detected input from the hardware to the micro-app.

In various embodiments, the telemedicine management system 500 may include a software program stored in a memory of a computer, accessible through the Internet, or the like. In various embodiments, the software program of the telemedicine management system 500 is configured to perform the methods described herein in a memory (e.g., a local memory, a cloud-based memory, or the like) and run the software program using a processor of the first device 110 (e.g., a computer) and/or the second device 120 (e.g., a computer). The first device 110 and the second device 120 may each include any number of individual processors and memories. Various data (e.g., video data, sound data, etc.) may be communicated between the first device 110 of a local user 101 (e.g., a parent, a guardian, a patient 105, a local doctor, a local nurse, etc.) via the first UI 112 of the telemedicine management system 500, the portable medical device 200, and the second device 120 of the remote user 103 (e.g., a remote doctor, a remote nurse, etc.) via the second UI 122 of the telemedicine management system 500 as described further herein. For example, the first device 110 can be in electronic communication with the second device 120 through a network 130. Such information may also be communicated between the external devices (e.g., first device 110, and/or second device 120) through the telemedicine management system 500 by use of the network 130 (e.g., through any network 130 such as a local area network (LAN), or wide area network (WAN) such as the Internet).

As used herein, the term "network" includes any cloud, cloud computing system, or electronic communications system or method which incorporates hardware and/or software components. Communication among the parties may be accomplished through any suitable communication channels, such as, for example, a telephone network, an extranet, an intranet, internet, point of interaction device (point of sale device, personal digital assistant (e.g., an IPHONE® device, a BLACKBERRY® device), cellular phone, kiosk, etc.), online communications, satellite communications, off-line communications, wireless communications, transponder communications, local area network (LAN), wide area network (WAN), virtual private network (VPN), networked or linked devices, keyboard, mouse, and/or any suitable communication or data input modality. Moreover, although the system is frequently described herein as being implemented with TCP/IP communications protocols, the system may also be implemented using IPX, APPLETALK® program, IP-6, NetBIOS, OSI, any tunneling protocol (e.g. IPsec, SSH, etc.), or any number of existing or future protocols. If the network is in the nature of a public network, such as the internet, it may be advantageous to presume the network to be insecure and open to eavesdroppers. Specific information related to the protocols, standards, and application software utilized in connection with the internet may be contemplated.

"Cloud" or "Cloud computing" includes a model for enabling convenient, on-demand network access to a shared pool of configurable computing resources (e.g., networks, servers, storage, applications, and services) that can be rapidly provisioned and released with minimal management effort or service provider interaction. Cloud computing may include location-independent computing, whereby shared servers provide resources, software, and data to computers and other devices on demand.

As used herein, "transmit" may include sending electronic data from one system component to another over a network connection. Additionally, as used herein, "data" may include encompassing information such as commands, queries, files, data for storage, and the like in digital or any other form.

The telemedicine management system 500 may receive and display information (such as video data, selection devices to select cameras, etc.) via the first UI 112 and/or the second UI 122. The user interfaces (e.g., the first UI 112 and/or the second UI 122) may include various peripheral output devices (such as monitors and printers), as well as any suitable input or control devices (such as a mouse and keyboard) to allow users to control and interact with the software program.

In various embodiments, first device 110 and second device 120 may each be in electronic communication with telemedicine management system 500, directly or via a respective user interface (e.g., first UI 115 and/or second UI 125). First device 110 and second device 120 may comprise any suitable hardware, software, and/or database components capable of sending, receiving, and storing data. For example, first device 110 and/or second device 120 may comprise a personal computer, personal digital assistant, cellular phone, smartphone (e.g., IPHONE®, BLACKBERRY®, and/or the like), IoT device, telehealth device, and/or the like. First device 110 and/or second device 120 may comprise an operating system, such as, for example, a WINDOWS® mobile operating system, an ANDROID® operating system, APPLE® IOS®, a BLACKBERRY® operating system, a LINUX® operating system, and the like. First device 110 and/or second device 120 may also comprise software components installed on first device 110 and/or second device 120 and configured to enable access to various telemedicine management system 500 components. For example, first device 110 and/or second device 120 may comprise a web browser (e.g., MICROSOFT INTERNET EXPLORER®, GOOGLE CHROME®, etc.), an application, a micro-app or mobile application, or the like, configured to allow the first device 110 and/or the second device 120 to access and interact with telemedicine management system 500 (e.g., directly or via a respective UI, as discussed further herein).

In various embodiments, first device 110 may be configured to communicate with and/or interact with telemedicine management system 500 via first UI 112. First UI 112 may comprise a graphical user interface (GUI) accessible via a mobile application, web browser, software application, or the like. For example, first device 110 may interact with first UI 112 to instruct telemedicine management system 500 to electronically couple the portable medical device 200 to the telemedicine management system 500 (e.g., through a first router 114 or directly). In this regard, as described further herein, video data from a camera of the portable medical device 200 can be transmitted from the portable medical device 200 to the first device 110 through the telemedicine management system 500. Further, as will be discussed further herein, the video data from the portable medical device 200 can be shared by the local user 101 through the first UI 112 of the telemedicine management system 500 across the network 130 to remote user 103 through the second UI 122 of the telemedicine management system 500 displayed on the second device 120, which can be connected to the network 130 through router 124. Accordingly, the telemedicine system 100 and the telemedicine management system 500 disclosed herein are configured to transmit video data from a portable medical device 200 (e.g., video data of a patient 105) from a first location (e.g., a location of the local user 101 and the patient 105) to a second location (i.e., a remote location of a remote user 103).

In various embodiments, the telemedicine management system 500 disclosed herein is configured to facilitate a telehealth visit where basic examinations (i.e., such as those typically performed in a doctors office) can be performed. For example, as will be discussed in more detail further herein, the portable medical device 200 can be configured with an otoscope to perform an ear inspection of the patient 105 and/or a general camera with a fixed magnification configured to record (or stream) video data from a general examination (e.g., of the throat or nose of the patient 105).

In various embodiments, the portable medical device 200 can be operated by the patient 105 directly or a user (e.g., a parent, a guardian, a significant other, a sibling, nurse, etc.). Similarly, either the local user 101 or the patient 105 can operate the first UI 112 of the telemedicine system 300 to ensure communication with the remote user 103 as described further herein.

Figure 2A:
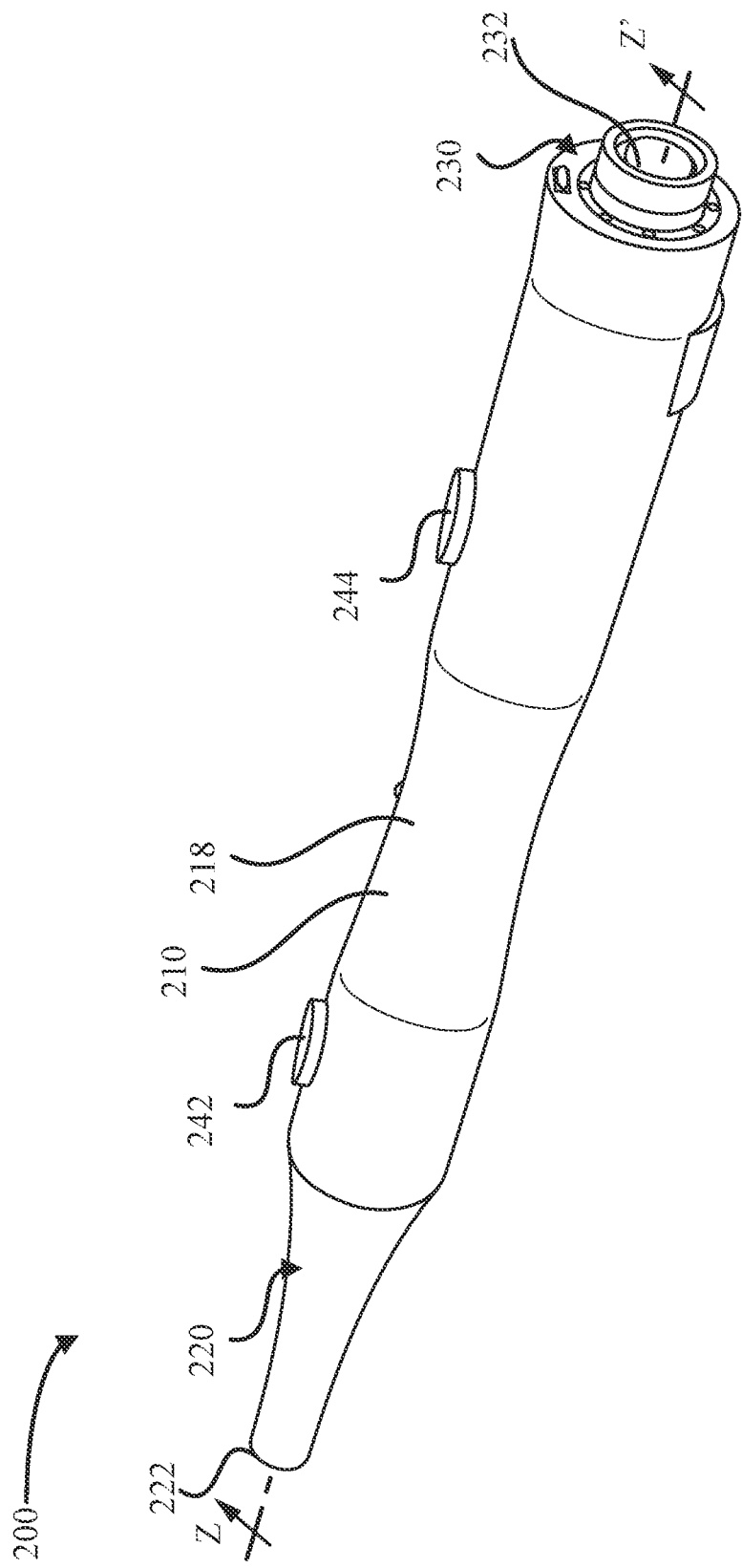
FIG. 2A illustrates a perspective view of a portable medical device for use in a telemedicine system, in accordance with various embodiments.
Figure 2B:
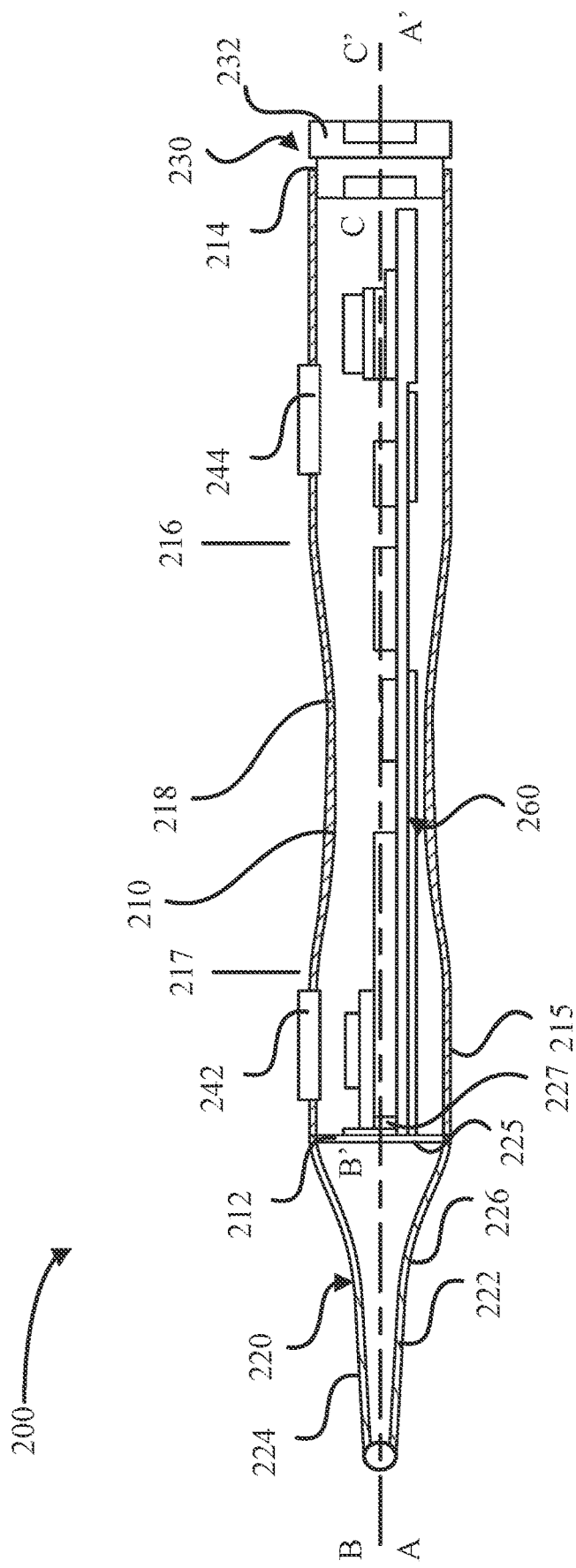
FIG. 2B illustrates a cross-sectional view of the portable medical device of FIG. 2A, in accordance with various embodiments.

Referring now to FIGS. 2A and 2B, a perspective view of a portable medical device 200 (FIG. 2A) and a cross-sectional view of the medical device 200 along section line Z-Z' (FIG. 2B) for use in a telemedicine system are illustrated, in accordance with various embodiments. The medical device 200 is configured for home use (e.g., by a parent, sibling, guardian, etc.), for use in an emergency situation (e.g., on an airplane, on a boat, etc.), or the like. The present disclosure is not limited in this regard. In various embodiments, the medical device 200 is configured to perform various functions associated with a telemedicine.

The medical device 200 comprises a main body 210 extending longitudinally from a first end 212 to a second end 214, a camera 220 disposed at the first end 212, and a camera 230 disposed at the second end 214. Although illustrated with dual cameras (i.e., cameras 220, 230), the present disclosure is not limited in this regard. For example, a medical device having only a single camera (e.g., only camera 220 or only camera 230) is within the scope of this disclosure.

The camera 220 can be configured with otoscopic lensing (i.e., lensing designed for inspecting an ear of a patient), and the camera 230 can be configured with general lensing (i.e., a general video scope configured for throat inspections, nose inspections or other general inspections). Accordingly, the medical device 200 can be configured for both general medical exams and otoscopic inspections and general inspections, in accordance with various embodiments.

In various embodiments, the main body 210 defines a longitudinal axis A-A'. For example, the main body 210 can define a centerline that corresponds to the longitudinal axis A-A'. Similarly, the camera 220 defines an optical axis B-B', and the camera 230 defines an optical axis C-C'. In various embodiments, the optical axis B-B' of the camera 220, and the optical axis C-C' are substantially parallel to the longitudinal axis A-A' of the main body 210. "Substantially parallel" as referred to herein, is parallel +/−10 degrees, or +/−5 degrees. In various embodiments, the optical axis B-B' of the camera 220 and the optical axis C-C' of the camera 230 are co-axial to each other. In various embodiments, the optical axis B-B' of the camera 220 and the optical axis C-C' of the camera 230 are co-axial with the longitudinal axis A-A'. In various embodiments, by having parallel and/or co-axial cameras 220, 230, the medical device 200 can be easier to manufacture relative to having optical axis which are non-parallel. In various embodiment, by having cameras 220, 230 parallel with the longitudinal axis A-A', the optical axis can be easily aligned by a user during use (e.g., by referencing a direction of the medical device 200).

In various embodiments, the main body defines a grip 218. For example, the main body 210 can comprise a varying cross-sectional diameter as the main body 210 extends from the first end 212 to the second end 214. In various embodiments, the grip 218 can be defined between a first axial location 216 and a second axial location 217. Between the first axial location 216 and the second axial location 217, the cross-sectional diameter of the main body 210 can decrease from a first diameter at the first axial location 216 to a minimum diameter (e.g., proximal a midpoint axially along the grip 218), and increase to second diameter at the second axial location 217. In this regard, the grip 218 can be configured to receive a hand to hold the portable medical device 200 in an ergonomic fashion.

In various embodiments, the main body 210 can comprise a membrane 215. For example, the membrane 215 can be thin and tactile (e.g., between 0.01 inches (0.025 cm) and 0.25 inches (0.635 cm), or between 0.01 inches (0.025 cm) and 0.225 inches (0.32 cm), or the like). In various embodiments, the membrane 215 can be an elastomeric material. In this regard, the membrane can be configured to cover harder components, such as a printed circuit board, a housing, and/or various internal components of the portable medical device 200 disposed within the main body 210. In various embodiments the membrane 215 is configured to provide a soft exterior for gripping for an ergonomic benefit to users, in accordance with various embodiments.

In various embodiments, the camera 220 comprises a lens 222. The lens 222 can include a fixed magnification. For example, the lens 222 can comprise a lens having a fixed magnification between 15× and 20×, or approximately 18×. In various embodiments, the lens 222 is distinct form the camera 220. In various embodiments, the lens 222 is an otoscopic lens 224. For example, the otoscopic lens 224 can comprise a magnifying lens 225, a speculum 226, and a light source 227. The speculum 226 of the otoscopic lens 224 can be detachable and include an insert configured to press fit into an aperture at the first end 212 of the main body 210. In this regard, the speculum 226 otoscopic lens 224 can be coupled to the lens to the main body 210 in an easy and straightforward manner, in accordance with various embodiments. Although described as being detachable, the speculum 226 is not limited in this regard. For example, the speculum 226 of the otoscopic lens 224 can be integral (i.e., form one monolithic piece) with the main body 210 and be within the scope of this disclosure.

In various embodiments, the camera 230 comprises a video scope 232 configured for adjustable magnification of an object. For example, video scope 232 of the camera 230 can comprise a 2×-4× near-far general video scope, a 0.5×-2×—near-far general video scope, or the like. The present disclosure is not limited in this regard.

In various embodiments, the portable medical device 200 further comprises a button 242 and a button 244. The button 242 is electronically (e.g., wired or wirelessly) coupled to the camera 220. Similarly, the button 244 is electronically coupled the camera 230. In various embodiments, the grip 218 is disposed axially between the button 242 and the button 244. In this regard, a thumb of a user can be oriented towards a button that controls a camera that the user is using. For example, in response to using the camera 220, a field of view of the camera 220 will be directed in an axial direction away from the main body 210 of the medical device 200. Accordingly, a user's hand will be around the grip 218 and a thumb of the user will be oriented towards button 242, which controls the camera 220. Similarly, in response to using camera 230, a field of view of the camera 230 will be directed in an axially opposite direction from the camera 220. In this regard, a user's hand will be oriented in an opposite direction from the axial direction when the camera 220 is in use. Accordingly, a thumb of the user's hand will be oriented towards the button 244, which controls the camera 230.

In various embodiments, the button 242 is configured to freeze a frame of the camera 220 in response to being depressed. For example, when video data from the camera 220 is being fed to a doctor (e.g., via a telemedicine system as described further herein), the doctor may want the patient to pause the camera 220 to take a closer look, or to capture an image. In this regard, the patient, or a local person working with the patient, can press the button 242 and freeze a frame of the camera 220, in accordance with various embodiments. Similarly, the button 244 can be configured to freeze a frame of the camera 230 for similar reasons, in accordance with various embodiments.

In various embodiments, the portable medical device 200 further comprises a plurality of lights 252 disposed circumferentially around the camera 220. In various embodiments, each light in the plurality of lights 252 can comprise a light emitting diode ("LED"), an incandescent light, a compact fluorescent light ("CFL"), a halogen light, or the like. The present disclosure is not limited in this regard. In various embodiments, each light in the plurality of lights comprises an LED. In various embodiments, the LED can be configured to emit an electromagnetic radiation with an average wavelength between 780 nm and 1 mm (i.e., an infrared LED). In various embodiments, each light in the plurality of lights includes a color temperature between 3700K and 4700K, or approximately 4300K. In this regard, the plurality of lights 252 can be configured to emit a bright white color to illuminate an object being inspected by the portable medical device 200.

In various embodiments, the portable medical device 200 further comprises an electronic system 300. For example, the electronic system 260 can comprise a printed circuit board 262 disposed within the main body 210 of the portable medical device 200. In this regard, the printed circuit board 262 can include various electrical components of the portable medical device 200, in accordance with various embodiments.

In various embodiments, the electronic system 260 is configured to facilitate communications between the portable medical device 200 and a telemedicine management system of a telemedicine system. In this regard, the electronic system 260 is configured to transmit video data from cameras 220, 230, in accordance with various embodiments. In various embodiments, the telemedicine management system can be capable of controlling various aspects of the portable medical device 200 (e.g., freezing a frame of a camera, zooming in or out with the camera, or the like). The present disclosure is not limited in this regard.

Figure 2C:
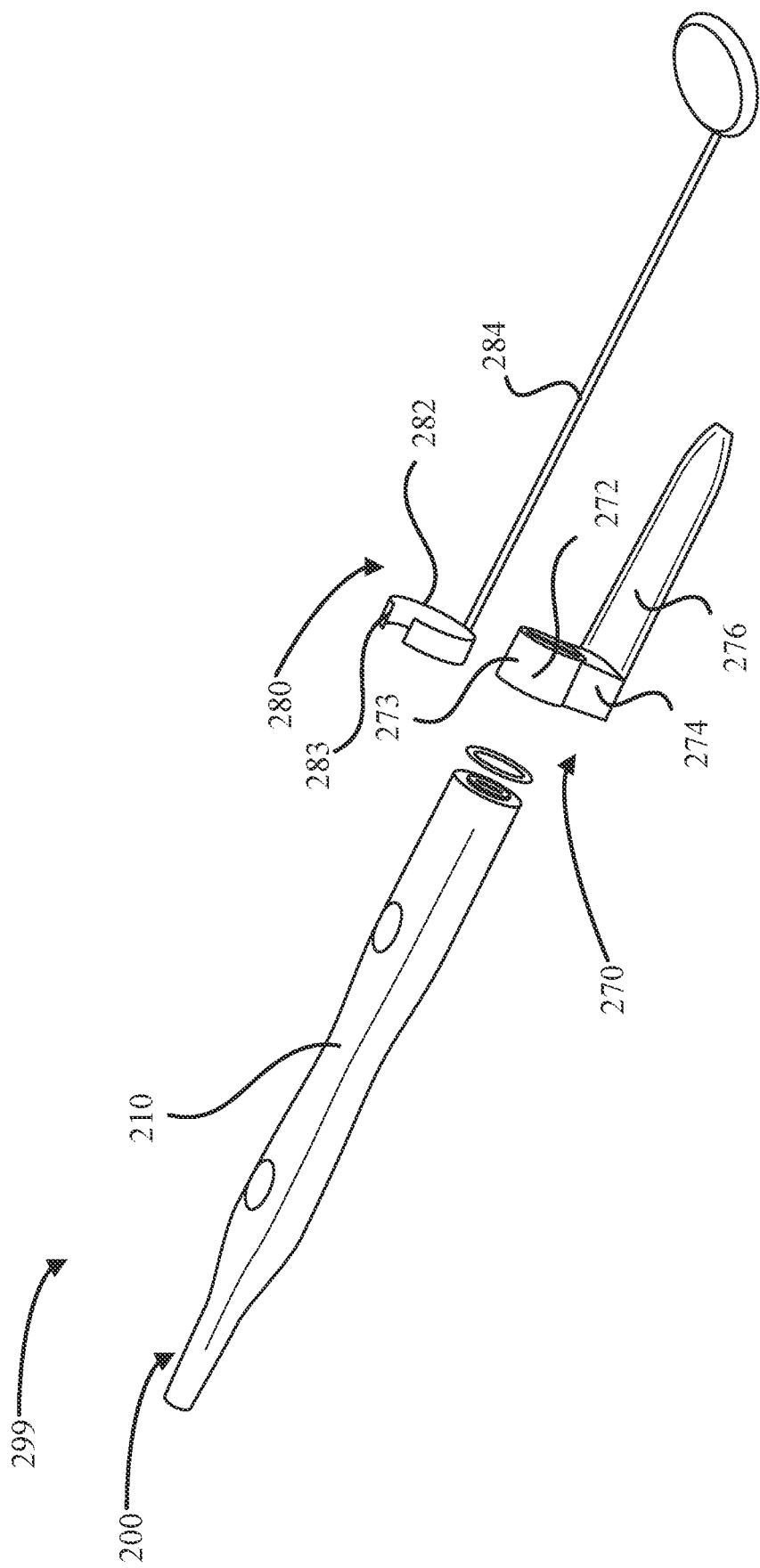
FIG. 2C illustrates a perspective view of a portable medical kit having a portable medical device, in accordance with various embodiments.

Referring now to FIG. 2C, an exploded view of a portable medical kit 299 is illustrated, in accordance with various embodiments. The portable medical kit 299 includes the portable medical device 200 and detachable components (e.g., a tongue depressor 270 and an extended mirror 280). In this regard, the portable medical device 200 can be adaptable by coupling a detachable component to the main body 210 of the portable medical device 200. For example, the tongue depressor 270 can include an attachment feature 272 configured to couple to the main body 210 of the portable medical device 200. In various embodiments, the attachment feature 272 can comprise an annular ring 273 configured to be coupled to an outer surface of the main body 210 (e.g., via a press fit or the like). Although illustrated being an annular ring 273 configured to create a press fit with the main body 210 to detachably couple the tongue depressor 270 to the main body 210, the present disclosure is not limited in this regard. For example, the attachment feature 272 can include a clamp, a spring, a fastener, or the like and still be within the scope of this disclosure.

In various embodiments, the tongue depressor 270 comprises a mount 274 extending outward from the attachment feature 272 and an elongated member 276 extending axially from the mount 274. In various embodiments, the elongated member 276 is configured to depress a tongue of a patient (e.g., patient 105 from FIG. 1).

In various embodiments, the extended mirror 280 includes an attachment feature 282. In various embodiments, the attachment feature 282 can comprise a clamp 283 (e.g., a snap-fit clamp). Although illustrated as comprising a clamp, any attachment feature configured to couple the extended mirror 280 to the main body 210 of the medical device 200 is within the scope of this disclosure. For example, the attachment feature 282 can comprise an annular ring configured to be press fit to the outer surface of the main body 210, a fastener, a spring, or the like.

In various embodiments, the extended mirror 280 further comprises a rod 284 extending axially from the attachment feature 282 to a mirror 286. In various embodiments, a plane defined by a surface of the mirror 286 forms an obtuse angle with a centerline defined by the rod 284. In this regard, the mirror 286 can be configured to redirect a view of the camera 230, in response to being coupled to the main body 210 of the portable medical device 200, in accordance with various embodiments.

Figure 3:
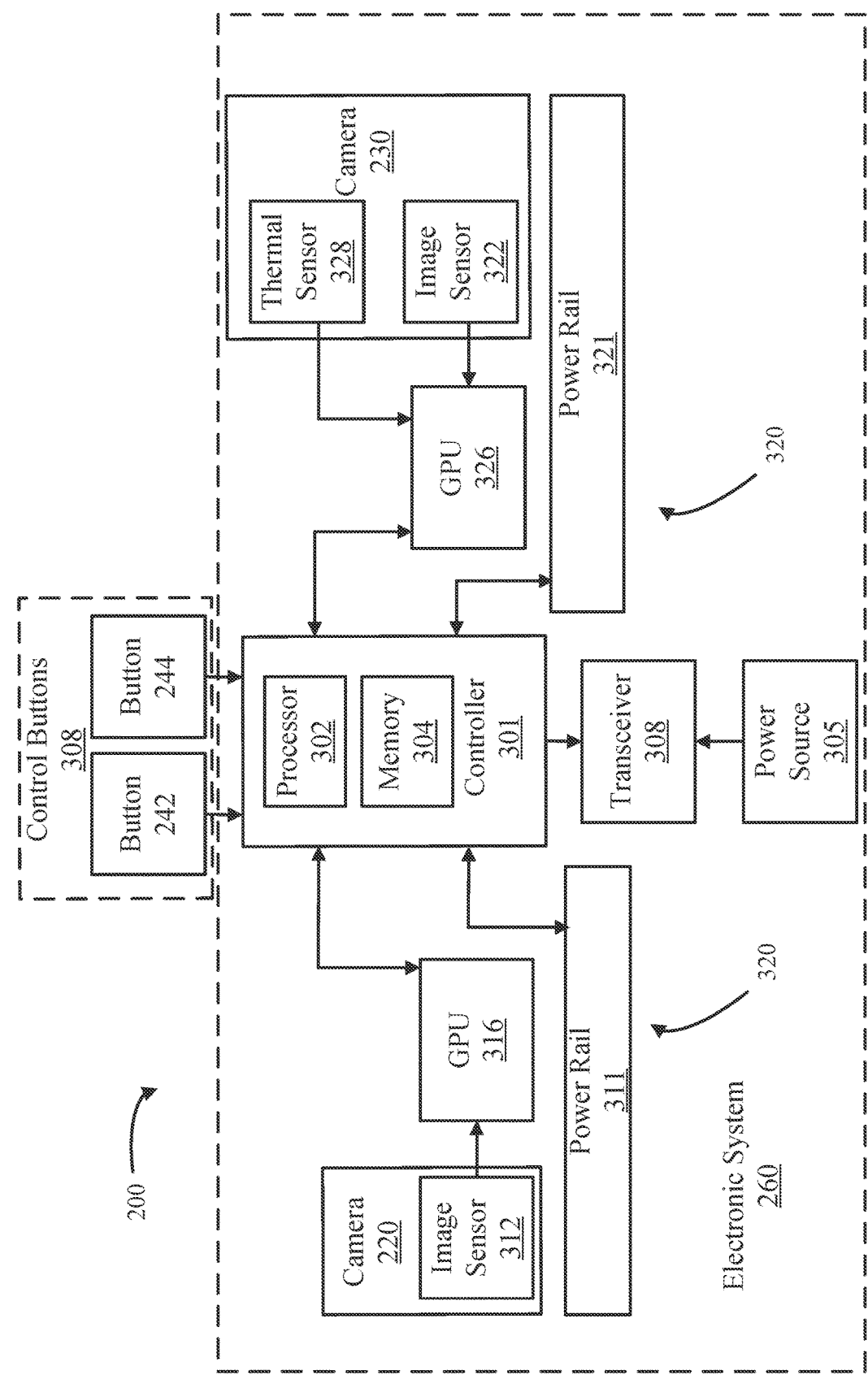
FIG. 3 illustrates an electronic system of a portable medical device, in accordance with various embodiments.

Referring now to FIG. 3, a schematic view of the electronic system 260 of the portable medical device 200 from FIG. 2 is illustrated, in accordance with various embodiments. As described further herein, the electronic system 260 is configured to interface with the telemedicine management system 500 from FIG. 1. In this regard, the electronic system 260 is configured to facilitate a telehealth visit through telemedicine system 100 of FIG. 1. For example, the electronic system 260, as described further herein is configured to transmit video data from the camera 220 and/or the camera 230 from the portable medical device 200 to the first device 110 and to the second device 120 through the telemedicine management system 500 as shown in FIG. 1.

In various embodiments, the electronic system 260 comprises a controller 301, control buttons 306, a transceiver 308, at least one sensor (e.g., image sensor 312 of camera 220, image sensor 322 of camera 230, and/or thermal sensor 328 of camera 230), a graphical processing unit (GPU) associated with each camera (e.g., GPU 316 for camera 220 and GPU 326 for camera 230), and a power source 305. In various embodiments, the controller 301 comprises a processor 302 and a memory 304.

In various embodiments, the controller 301 is configured as a central network element or hub to various systems and components of the electronic system 260. In various embodiments, controller 301 comprises a processor (e.g., processor 302). In various embodiments, controller 301 may be implemented as a single controller (e.g., via a single processor 302 and associated memory 304). In various embodiments, controller 301 may be implemented as multiple processors (e.g., a main processor and local processors for various components). The controller 301 can be a general purpose processor, a digital signal processor (DSP), an application specific integrated circuit (ASIC), a field programmable gate array (FPGA) or other programmable logic device, discrete gate or transistor logic, discrete hardware components, or any combination thereof. The controller 301 may comprise a processor 302 configured to implement various logical operations in response to execution of instructions, for example, instructions stored on a non-transitory, tangible, computer-readable medium (e.g., memory 304) configured to communicate with the controller 301. System program instructions and/or controller instructions may be loaded onto a non-transitory, tangible computer-readable medium (e.g., memory 304) having instructions stored thereon that, in response to execution by a controller 301, cause the controller 301 to perform various operations.

In various embodiments, the controller 301 is a component of a management system for the cameras 220, 230. In various embodiments, the management system can further comprise a direct device point-point communications setup. In various embodiments, the management system can be configured for battery management and battery life feedback of the cameras 220, 230 (e.g., via the controller 301). In various embodiments, the management system can be configured to determine a light level of the cameras 220, 230.

In various embodiments, each camera comprises an image sensor. For example, camera 220 comprises image sensor 312 and camera 230 comprises image sensor 322. In various embodiments, the camera 230 can further comprise a thermal sensor 328. In this regard, the camera 230 can be further configured for thermal imaging as a part of a medical exam, in accordance with various embodiments. In various embodiments, the thermal sensor 328 comprises an infrared sensor. For example, the thermal sensor 322 can comprise a FLIR 80×120 infrared sensor, in accordance with various embodiments. In various embodiments, the image sensors 312, 322 can be any image sensor known in the art. In various embodiments, the image sensors 312, 322 can comprise 1080p/60 OnmiVision sensors. However, the present disclosure is not limited in this regard.

In various embodiments, each sensor of a respective camera in the electronic system 260 is in electronic communication with the controller 301 through a graphical processing unit. For example, the image sensor 312 is in electronic communication with the controller 301 through the GPU 316. Similarly, the image sensor 322 and the thermal sensor 328 are in electronic communication with the controller 301 through the GPU 326. In various embodiments, GPUs 316, 326 can comprise any graphical processing unit for processing video data. In various embodiments, GPUs 316, 326 can each include a video processing engine and a video converter (e.g., an h.264 engine). Although described herein with an h.265 encoder, the present disclosure is not limited in this regard. Any encoder configured to reduce a video size is within the scope of this disclosure.

In various embodiments, the control buttons 306 (e.g., buttons 242, 244 from FIGS. 2A and 2B) are configured to control various aspects of the cameras 220, 230. For example, in response to pressing and releasing the button 242, the image sensor 312 can be transitioned from an "OFF" state to an "ON" state. In this regard, the image sensor 312 can begin to capture video data. In various embodiments, by holding the button 242, a frame of the image sensor 312 can freeze, to hold an image captured by the image sensor 312 (e.g., for a remote user 103 from FIG. 1 to review during a telehealth visit with telemedicine system 100 from FIG. 1). In various embodiments, pressing and releasing the button 242 can transition the image sensor 312 back from the ON state to the OFF state. Although described herein as comprising a single button, the present disclosure is not limited in this regard. For example, the portable medical device 200 can comprise multiple control buttons 308 for each camera to control various aspects of the camera and still be within the scope of this disclosure. For example, a freeze button can be separate from a ON/OFF button, in accordance with various embodiments.

In various embodiments, the electronic system 300 further comprises a transistor circuit 320. The transistor circuit 320 comprises power rail 311 (e.g., a positive voltage current collector (Vcc) power rail) and power rail 321 (e.g., a negative Vcc power rail). The transistor circuit 320 can be configured to determine a body temperature of a patient (e.g., patient 105 from FIG. 1). For example, in response to a patient 105 from FIG. 1 placing a hand in contact with the power rail 311 and the power rail 321, the transistor circuit 320 can determine a body temperature of the patient 105 and transmit the body temperature data to the controller 301, in accordance with various embodiments. In this regard, the body temperature data can be transmitted to the remote user 103 from FIG. 1 through the telemedicine management system 500 from FIG. 1 as described further herein and in accordance with various embodiments.

In various embodiments, the controller 301 is in electronic communication (e.g., wirelessly or wired and either directly or indirectly) with the image sensor 312, the image sensor 322, the thermal sensor 328, and the transceiver 308 (e.g., a WiFi Module with the transceiver 308 and/or a radio module with the transceiver 308, or the like). Although illustrated as having a single transceiver 308, the present disclosure is not limited in this regard. For example, the electronic system 260 can include two transmitters (e.g. a WiFi module with a first transmitter and a radio module with a second transmitter), in accordance with various embodiments. In various embodiments, by having a WiFi module and a radio module, the electronic system 260 can be configured to transmit data from the portable medical device 200 directly to a user device (e.g., directly to first device 110 from FIG. 1) or to a user device through a network (e.g., through router 114 from FIG. 1), in accordance with various embodiments. The present disclosure is not limited in this regard.

Although described herein as comprising a transceiver 308, the present disclosure is not limited in this regard. For example, the electronic system 260 can comprise a transmitter and a receiver as separate components and still be within the scope of this disclosure.

Figure 4A:
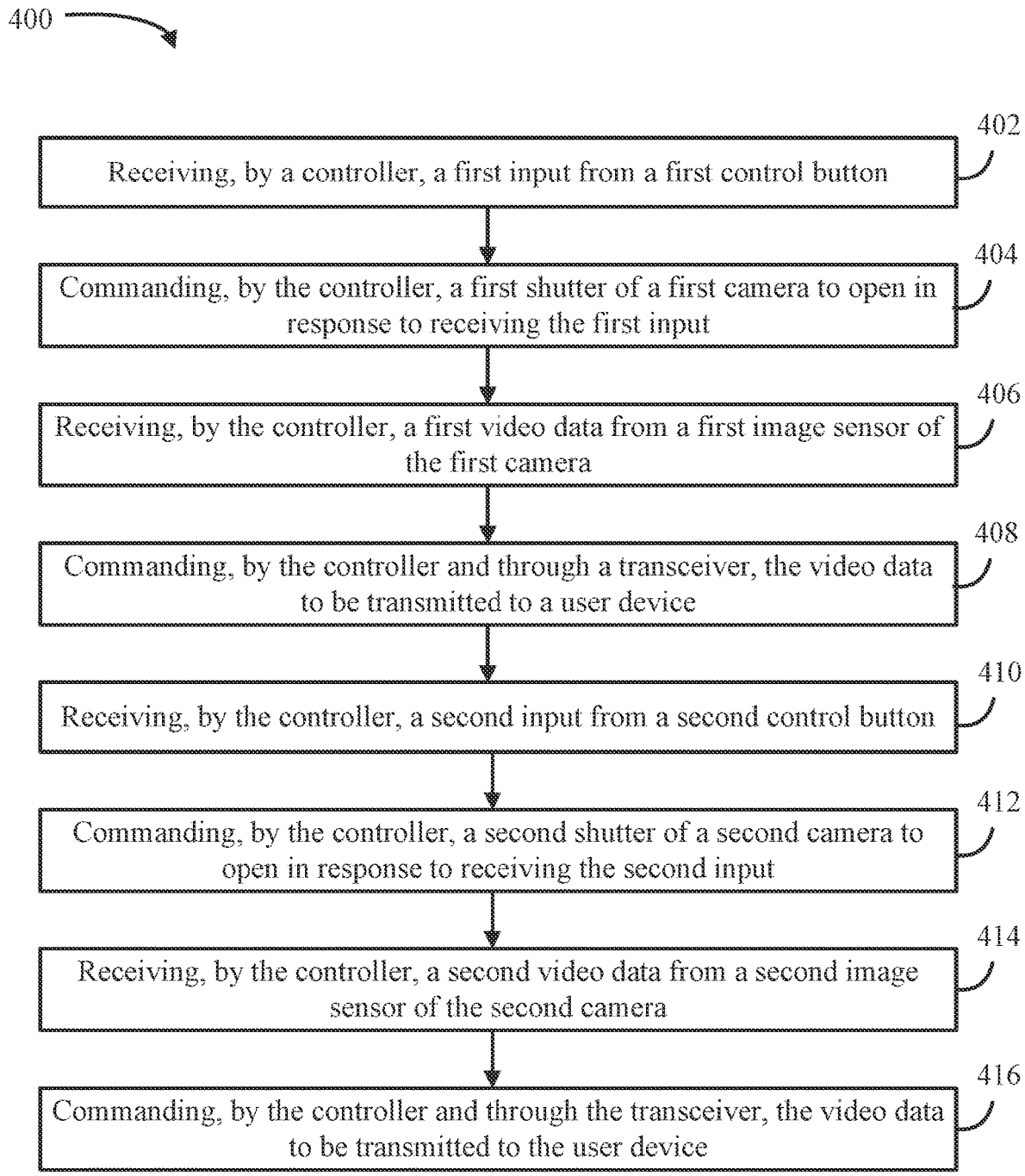
FIG. 4A illustrates a process performed by the electronic system of FIG. 3, in accordance with various embodiments.

Referring now to FIG. 4A, a process 400 that can be performed by the electronic system 260 from FIG. 3 is illustrated, in accordance with various embodiments. With combined reference to FIGS. 3 and 4, the process 400 comprises receiving, by the controller 301, a first input from a first control button (e.g., button 242) (step 402). As described previously herein, the controller 301 can be configured to transition the image sensor 312 of the camera 220 from an OFF state to an ON state in response to receiving an input from the button 242. An "OFF state" as disclosed to herein refers to the image sensor 312 being obstructed (e.g., by a shutter or the like). In this regard, in the OFF state, the image sensor 312 is not exposed to light. An "ON state" s disclosed herein refers to the image sensor 312 being un-obstructed, or partially obstructed. In this regard, in the ON state, the image sensor 312 is exposed, or at least partially exposed.

In various embodiments, in response to receiving the first input in step 402, the process 400 further comprises commanding, by the controller a first shutter of a first camera (e.g., camera 220) to open (step 404). In this regard, the image sensor 312 of the camera 220 is exposed, or at least partially exposed to light. In response to the image sensor 312 being exposed to light, the image sensor converts the light waves into electrical signals that are transmitted to the controller 301 through the GPU 316. In various embodiments, the GPU 316 can be configured to reduce a size of the video data received from the image sensor, in accordance with various embodiments.

In various embodiments, the process 400 further comprises receiving, by the controller 301, a first video data from the first image sensor (e.g., image sensor 312) of the first camera (e.g., camera 220) (step 406). As described herein, the video data can be reduced in size via the GPU 316 prior to being received by the controller 301. In various embodiments, the video data passes through a shared frame buffer and pass-through of the controller 301 (e.g., in memory 304). In various embodiments, the frame buffer and pass through can convert an in-memory bitmap into a video signal that can be transmitted, and displayed, on a device (e.g., first device 110 from FIG. 1).

In various embodiments, the process 400 further comprises commanding, by the controller 401 and through a transceiver 308 (e.g., of a WiFi module or a radio module), the video data to be transmitted to a user device (e.g., first device 110 from FIG. 1) (step 408). In various embodiments, the video data can be transmitted in response to receiving a video request from a telemedicine management system 500 from FIG. 1 as described further herein. In this regard, in response to the telemedicine management system 500 requesting video data from the portable medical device (e.g., through the transceiver 308), step 408 is performed by the controller 301 as described further herein.

In various embodiments, the process 400 further comprises receiving by the controller 301, a second input from a second control button (e.g., button 244) (step 410). In various embodiments, in response to receiving the second input from the second control button, the image sensor 322 associated with the button 244 can transition from an OFF state to an ON state and the image sensor 312 associated with the button 242 can transition from the ON state to the OFF state. In this regard, pressing the button 244 when the camera 220 associated with the button 242 is active can de-activate the camera 220 and activate the camera 230. In various embodiments, the button 242 may be used to deactivate the camera 220 prior to activating the camera 230 in accordance with step 410. The present disclosure is not limited in this regard.

In various embodiments, the process 400 further comprises commanding, by the controller 301, a second shutter of a second camera (e.g., camera 230) to open in response to receiving the second input (step 412). In this regard, the image sensor 322 of the camera 230 is exposed, or at least partially exposed to light. In response to the image sensor 322 being exposed to light, the image sensor 322 converts the light waves into electrical signals that are transmitted to the controller 301 through the GPU 326. In various embodiments, the GPU 326 can be configured to reduce a size of the video data received from the image sensor, in accordance with various embodiments.

In various embodiments, the process 400 further comprises receiving, by the controller 301, a second video data from the second image sensor of the second camera (step 414). As described herein, the video data can be reduced in size via the GPU 316 prior to being received by the controller 301. In various embodiments, the video data passes through a shared frame buffer and pass-through of the controller 301 (e.g., in memory 304). In various embodiments, the frame buffer and pass through can convert an in-memory bitmap into a video signal that can be transmitted, and displayed, on a device (e.g., first device 110 from FIG. 1).

In various embodiments, step 414 can further comprise receiving thermal imaging data from a thermal sensor 328 in response to receiving the second input in step 412. In this regard, the thermal imaging data can include data received from an infrared sensor. The thermal imaging data can pass through the GPU 326 in a similar manner to the second video data described previously herein.

In various embodiments, the process 400 further comprises commanding, by the controller 310 and through the transceiver 308, the second video data can be transmitted to the user device (e.g., first device 100) (step 416). In various embodiments, the second video data can be transmitted to the user device in a similar manner to transmission of the first video data as described in step 408. In this regard, the video data can be requested from a telemedicine management system 500 from FIG. 1, in accordance with various embodiments. In various embodiments, the thermal imaging data can be transferred with, or separate from, the second video data. The present disclosure is not limited in this regard.

Figure 4B:
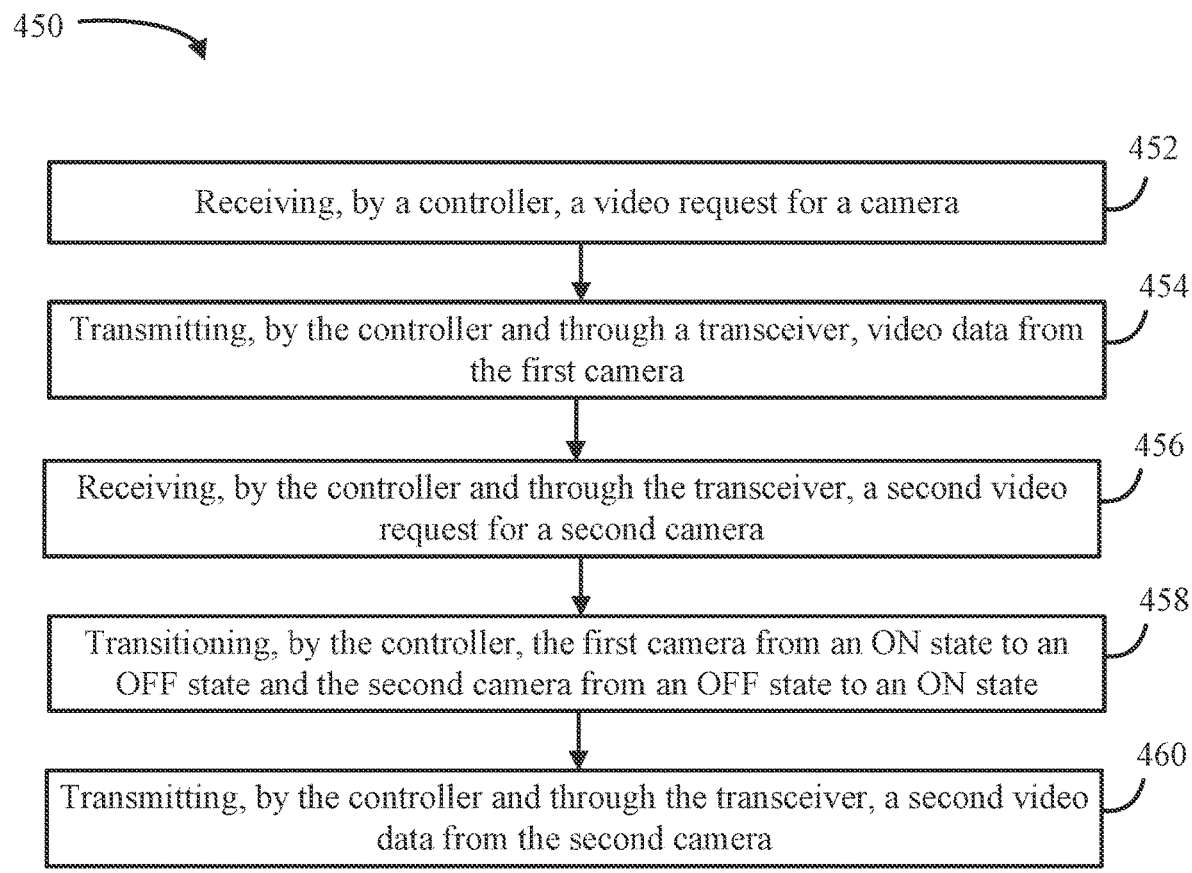
FIG. 4B illustrates a process performed by the electronic system of FIG. 3, in accordance with various embodiments.

Referring now to FIG. 4B, a process 450 performed by the controller 301 of the electronic system 260 (e.g., a control system) is illustrated, in accordance with various embodiments. With combined reference to FIGS. 3 and 4B, the process 450 comprises receiving, by the controller 301 and through a transceiver 308, a video request for a camera (step 452). In various embodiments, the video request may be generated through a user interface (e.g., first UI 112) of telemedicine management 500 from FIG. 1. For example, as described further herein, the first UI 112 can allow a user to select a camera (e.g., camera 220 or camera 230) of the portable medical device 200. In this regard, in response to a specific camera being selected, the telemedicine management system 500 can transmit a video request to the portable medical device 200, and the controller 301 receives the request in step 452.

In various embodiments, the process 450 further comprises transmitting, by the controller and through the transceiver 308, video data from the selected camera (e.g., camera 220 or camera 230) (454). In various embodiments, the camera can be transitioned from an OFF state to an ON state prior to transmitting the video data, in accordance with various embodiments. In various embodiments, the state of the camera that is selected can be determined by a corresponding button (e.g., button 242 for camera 220 or button 244 for camera 230). The present disclosure is not limited in this regard. In various embodiments, step 454 further comprises commanding, by the processor and through the transceiver 308, the video data from the image sensor 312 of the t camera 220 of the portable medical device 200 be transmitted to the telemedicine management system 500 (e.g., directly via a radio module or indirectly through a router via a WiFi module). In various embodiments, in response to the first video data being transmitted, the first video data can be sent through the telemedicine management system 500 to a remote user device (e.g., second device 120 from FIG. 1).

In various embodiments, the video request in step 452 can be a real time streaming protocol ("RTSP") request. In this regard, in response to a camera being selected in the telemedicine management system 500, as described further herein, a RTSP connection can be generated between the portable medical device 200 and the telemedicine management system 500 (e.g., through a router 114 or directly through a radio module). In this regard, prior to step 454, the RTSP can be setup between the first device 110 from FIG. 1 and the portable medical device 200. In various embodiments, RTSP can allow a local user 101 or patient 105 to stream video from a selected camera (e.g., camera 220 or camera 230) of the portable medical device 200 in real time. Although described herein as including RTSP, the present disclosure is not limited in this regard. Any streaming protocol can be used and is within the scope of this disclosure. For example, HTTP live streaming HLS), dynamic adaptive streaming over HTTP, secure reliable transport (SRT), or the like can be used and is within the scope of this disclosure.

In various embodiments, the process 450 further comprise receiving, by the controller 301 and through the transceiver 308, a second video request for a second camera (e.g., camera 230) (step 456). For example, a user (e.g., a local user 101 or a patient 105 from FIG. 1) can select a camera through the first UI 112 of the telemedicine management system 500 can select a different camera of the portable medical device 200 (e.g., transition from camera 220 to camera 230 or vice versa), and the telemedicine management system 500 can transmit a second video request to the portable medical device 200 in response to the selection. In response to the transmission by the telemedicine management system, the second video request can be received in step 456. Stated another way, the controller 301 receives an indication that a second camera has been selected by a user (e.g., local user 101 or patient 105 from FIG. 1).

In various embodiments, the process 450 further comprises transitioning, by the controller 301, the first camera from an ON state to an OFF state and the second camera from an OFF state to an ON state (step 458). In this regard, the controller 301 can de-activate the camera that is no longer selected and activate the camera that is selected, in accordance with various embodiments.

In various embodiments, the process 450 further comprises transmitting, by the controller 301 and through the transceiver 308, video data from the selected camera (e.g., camera 220 or camera 230) (step 460). Stated another way, step 454 is repeated for the newly selected camera. In various embodiments, the previously selected camera is deactivated prior to the newly selected camera being activated.

In various embodiments, a first set of the second video data received by the controller 301 and a second set of video data received by the controller 301 can be different magnifications. For example, as described previously herein, camera 230 can comprise a video scope configured to vary a magnification of a lens of the camera 230. In response to the magnification being varied, a magnification of the video data received from the camera 230 can vary. Accordingly, a local user 101 or a patient 105 from FIG. 1 can vary a magnification as requested by a remote user 103 during a telehealth visit via telemedicine system 100 from FIG. 1, in accordance with various embodiments.

In various embodiments, during transmitting of the video data of the selected camera in steps 454 and 458, a local user 101 or patient 105 from FIG. 1 can control aspects of the video data being transmitted via a button of the selected camera (e.g., button 242 for camera 220 or button 244 for camera 230). In this regard, in various embodiments, the process 454 can further include freezing, by the controller 301, a frame of the first video data in response to a button (e.g., button 242 or button 244) being depressed. In various embodiments, by holding the button, the frame of the video can be frozen, and the frozen frame can be transmitted to the telemedicine management system in accordance with step 454.

Figure 5:
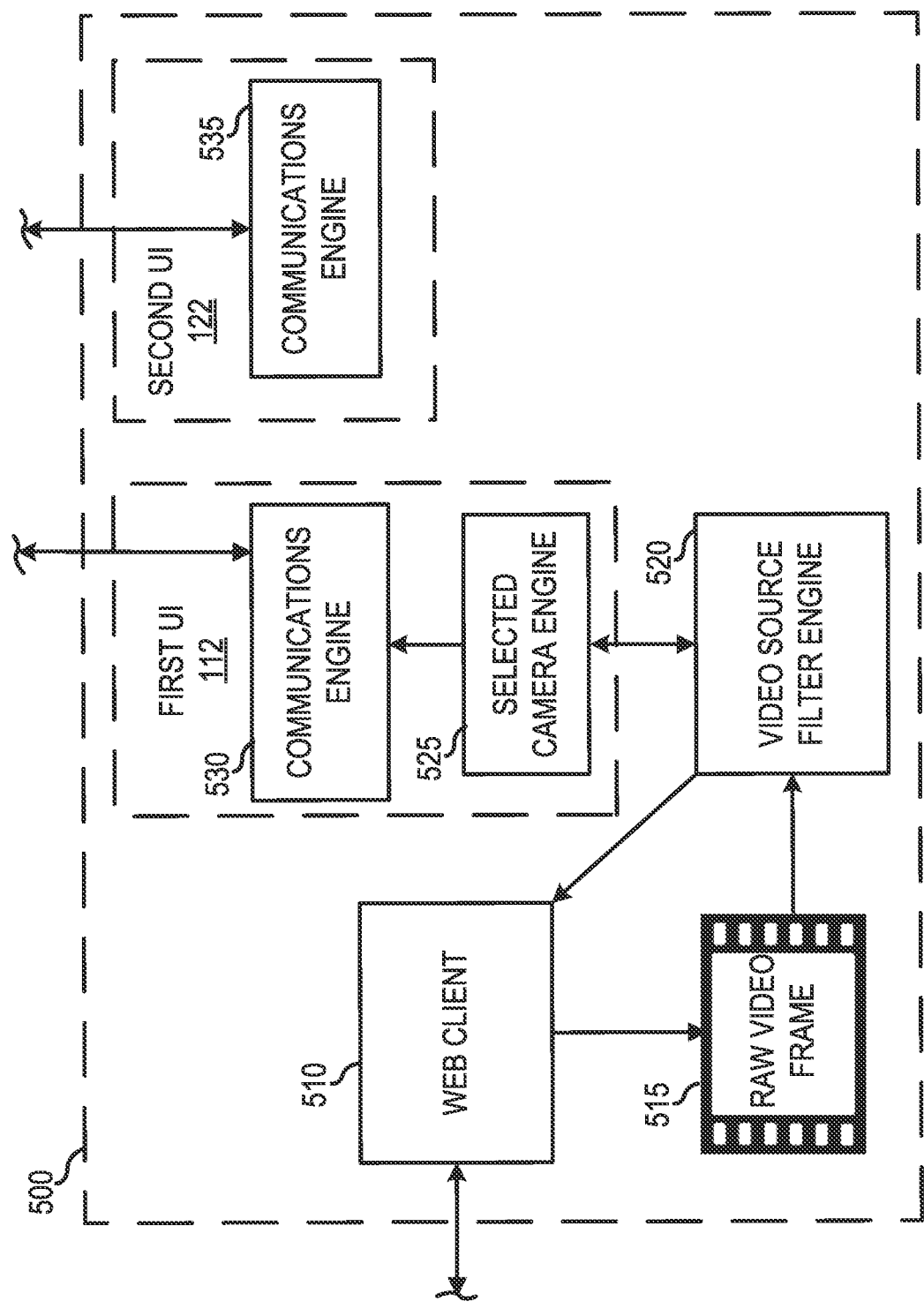
FIG. 5 illustrates a schematic view of a telemedicine management system, in accordance with various embodiments.

Referring now to FIG. 5, a schematic view of the telemedicine management system 500 from FIG. 1 is illustrated, in accordance with various embodiments. In various embodiments, the telemedicine management system comprises a web client 510, a video source filter engine 520, a selected camera engine 525, and a communications engine for each user interface (e.g., a communications engine 530 for the first UI and a communications engine 535 for the second UI 122. In various embodiments, the selected camera engine 525 is associated with the first UI 112 (i.e., the user interface that is proximate the portable medical device 200).

In various embodiments, the web client 510 can include a dynamic link library (DLL). For example, the web client 510 can be configured to support specific operations of the telemedicine management system 500 as described further herein. In various embodiments, the DLL of the web client 510 can include a source code in a respective programming language (e.g., C++, python, JavaScript, etc.). The present disclosure is not limited in this regard.

In various embodiments, the web client 510 is configured to communicate electronically (e.g., wirelessly) with the portable medical device 200. For example, the web client 510 can be configured to generate a RTSP connection with the portable medical device 200 as described previously herein.

In various embodiments, the video source filter engine 520 is configured to decode raw video frames 515 received from the web client 510. In this regard, as described further herein, in response to the web client 510 receiving video data from the portable medical device 200, raw video frames 515 are transmitted to the video source filter engine 520 for decoding, and then communicated to the first UI 112, in accordance with various embodiments.

In various embodiments, the video source filter engine 520 can comprise any source filter capable of decoding a raw video frame 515 In various embodiments, the video source filter comprises an RTSP DirectShow source filter.

In various embodiments, the communications engine 530 of the first UI 112 and the communications engine 535 of the second UI 122 are configured to enable Web applications and sites (e.g., Internet browsers) to capture and stream video media. Stated another way, the communications engine 530, 535 make it possible to share video data and perform teleconferencing peer-to-peer, without having the other user install plug-ins or any other third-party software. In various embodiments, the communications engine 530, 535 comprises Web Real-Time Communications ("WebRTC"). However, the present disclosure is not limited in this regard. For example, the communications engine 530 can comprise Element, Librem Chat, Conduit Chat Server, gevent, Autobahn, or the like. The present disclosure is not limited in this regard.

Figure 6:
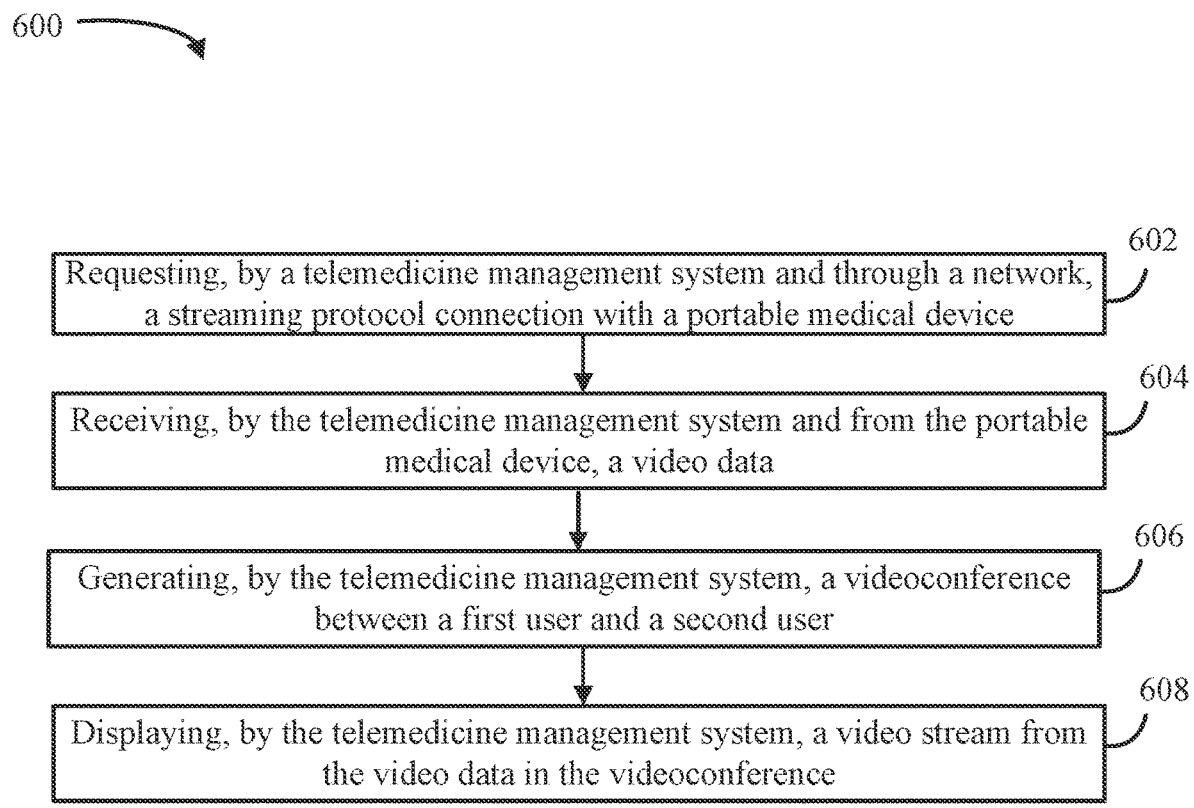
FIG. 6 illustrates a process performed by the telemedicine system, in accordance with various embodiments.

In various embodiments, the telemedicine management system 500 comprises a direct device point-to-point communications setup. In various embodiments, the telemedicine management system Referring now to FIG. 6, a process 600 performed by the telemedicine management system 500 from FIG. 5 is illustrated, in accordance with various embodiments. With reference now to FIGS. 1, 5, and 6, the process 600 comprises requesting, by the web client 510 of the telemedicine management system 500 and through a network 130, a streaming protocol (e.g., RTSP) connection with a portable medical device 200 (step 602). In various embodiments, a camera of the portable medical device 200 can be selected in the first UI 112 of the telemedicine management system 500 (e.g., via the selected camera engine 525) prior to step 602. In this regard, in response to selection of the camera, step 602 can be initiated. For example, corresponding source code of the web client 510 can receive a request from the video source filter engine 520 and begin a RTSP connection with the portable medical device 200 in response to receiving the request. Then, in response to the RTSP connection being established, the portable medical device 200 can send real-time transport (RTP) protocol packets carrying MP4 encoded video frames to the web client 510.

In this regard, the process 600 can further comprise receiving, by the web client 510 of the telemedicine management system 500, a video data from the portable medical device 200 (step 604). In various embodiments, the video data is transmitted as raw video frames 515 to the video source filter engine 520 to be decoded. The decoded video data from video source filter engine 520 is then sent to the first UI 112. In various embodiments, a media steam is created by a web browser on the first device 110, and the telemedicine management system 500 attaches the media stream to video elements from the video data to be displayed on the first device 110.

In various embodiments, the process 600 further comprises generating, by the communications engine 530, 535 the telemedicine management system 500, a videoconference between a first UI 112 of a first device and a second UI 122 of a second device 120 (step 606). In various embodiments, the video conference is generated via WebRTC API. In various embodiments, the web client 510 of the telemedicine management system 500 is configured to receive the video data from the portable medical device 200, the video source filter engine 520 is configured to decode the video data, the decoded video data is attached to a media stream created by an Internet browser, and the media stream can be added to the videoconference (e.g., the RTCPeerConnection), allowing the video stream to be included as a part of the videoconference.

In various embodiments, the process 600 further comprises displaying, by the telemedicine management system 500, a video stream from the video data in the videoconference (step 608). In this regard, the video stream can be shared by the local user 101 or the patient 105 to the remote user 103 by the video conference. In various embodiments, the video stream from the camera of the portable medical device 200 can be a second video stream being shared by the local user 101 and/or the patient 105 on the first device 110. For example, the video conference can include typical video sharing between a camera of first device 110 and a camera of second device 120. Similar, the video conference can include audio sharing between the first device 110 and the second device 120. For example, the process 600 can further comprise transmitting audio from the first device 110 to the second device 120 and/or transmitting audio from the second device 120 to the first device 110. In this regard, the patient 105 and/or the local user 101 can communicate with the remote user 103 during the telehealth visit, in accordance with various embodiments.

The system may allow users to access data and receive updated data in real time from other users. The system may store the data (e.g., in a standardized format) in a plurality of storage devices, provide remote access over a network so that users may update the data in a non-standardized format (e.g., dependent on the hardware and software platform used by the user) in real time through a GUI, convert the updated data that was input (e.g., by a user) in a non-standardized form to the standardized format, automatically generate a message (e.g., containing the updated data) whenever the updated data is stored and transmit the message to the users over a computer network in real time, so that the user has immediate access to the up-to-date data. The system allows remote users to share data in real time in a standardized format, regardless of the format (e.g. non-standardized) that the information was input by the user. The system may also include a filtering tool that is remote from the end user and provides customizable filtering features to each end user. The filtering tool may provide customizable filtering by filtering access to the data. The filtering tool may identify data or accounts that communicate with the server and may associate a request for content with the individual account. The system may include a filter on a local computer and a filter on a server.

The term "non-transitory" is to be understood to remove only propagating transitory signals per se from the claim scope and does not relinquish rights to all standard computer-readable media that are not only propagating transitory signals per se. Stated another way, the meaning of the term "non-transitory computer-readable medium" and "non-transitory computer-readable storage medium" should be construed to exclude only those types of transitory computer-readable media which were found in In re Nuijten to fall outside the scope of patentable subject matter under 35 U.S.C. § 101.

The process flows depicted are merely embodiments and are not intended to limit the scope of the disclosure. For example, the steps recited in any of the method or process descriptions may be executed in any order and are not limited to the order presented. It will be appreciated that the following description makes appropriate references not only to the steps and user interface (UI) elements, but also to the various system components as described herein. It should be understood that, although exemplary embodiments are illustrated in the figures and described herein, the principles of the present disclosure may be implemented using any number of techniques, whether currently known or not. The present disclosure should in no way be limited to the exemplary implementations and techniques illustrated in the drawings and described below. Unless otherwise specifically noted, articles depicted in the drawings are not necessarily drawn to scale.

Computer programs (also referred to as computer control logic) are stored in main memory and/or secondary memory. Computer programs may also be received via communications interface. Such computer programs, when executed, enable the computer system to perform the features as discussed herein. In particular, the computer programs, when executed, enable the processor to perform the features of various embodiments. Accordingly, such computer programs represent controllers of the computer system.

These computer program instructions may be loaded onto a general purpose computer, special purpose computer, or other programmable data processing apparatus to produce a machine, such that the instructions that execute on the computer or other programmable data processing apparatus create means for implementing the functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions specified in the flowchart block or blocks.

In various embodiments, software may be stored in a computer program product and loaded into a computer system using a removable storage drive, hard disk drive, or communications interface. The control logic (software), when executed by the processor, causes the processor to perform the functions of various embodiments as described herein. In various embodiments, hardware components may take the form of application specific integrated circuits (ASICs). Implementation of the hardware so as to perform the functions described herein will be apparent to persons skilled in the relevant art(s).

The systems and methods disclosed herein may be described in terms of functional block components, optional selections, and various processing steps. It should be appreciated that such functional blocks may be realized by any number of hardware and/or software components configured to perform the specified functions. For example, the system may employ various integrated circuit components, e.g., memory elements, processing elements, logic elements, look-up tables, and the like, which may carry out a variety of functions under the control of one or more microprocessors or other control devices. Similarly, the software elements of the system may be implemented with any programming or scripting language such as C, C++, C#, JAVA®, JAVASCRIPT®, JAVASCRIPT® Object Notation (JSON), VBScript, Macromedia COLD FUSION, COBOL, MICROSOFT® company's Active Server Pages, assembly, PERL®, PHP, awk, PYTHON®, Visual Basic, SQL Stored Procedures, PL/SQL, any UNIX® shell script, and extensible markup language (XML) with the various algorithms being implemented with any combination of data structures, objects, processes, routines or other programming elements. Further, it should be noted that the system may employ any number of techniques for data transmission, signaling, data processing, network control, and the like. Still further, the system could be used to detect or prevent security issues with a client-side scripting language, such as JAVASCRIPT®, VBScript, or the like.

The systems and methods described herein with reference to block diagrams and flowchart illustrations of methods, apparatus, and computer program products according to various embodiments. It will be understood that each functional block of the block diagrams and the flowchart illustrations, and combinations of functional blocks in the block diagrams and flowchart illustrations, respectively, can be implemented by computer program instructions.

Accordingly, functional blocks of the block diagrams and flowchart illustrations support combinations of means for performing the specified functions, combinations of steps for performing the specified functions, and program instruction means for performing the specified functions. It will also be understood that each functional block of the block diagrams and flowchart illustrations, and combinations of functional blocks in the block diagrams and flowchart illustrations, can be implemented by either special purpose hardware-based computer systems which perform the specified functions or steps, or suitable combinations of special purpose hardware and computer instructions. Further, illustrations of the process flows and the descriptions thereof may make reference to user WINDOWS® applications, webpages, websites, web forms, prompts, etc. Practitioners will appreciate that the illustrated steps described herein may comprise, in any number of configurations, including the use of WINDOWS® applications, webpages, web forms, popup WINDOWS® applications, prompts, and the like. It should be further appreciated that the multiple steps as illustrated and described may be combined into single webpages and/or WINDOWS® applications but have been expanded for the sake of simplicity. In other cases, steps illustrated and described as single process steps may be separated into multiple webpages and/or WINDOWS® applications but have been combined for simplicity.

In various embodiments, the software elements of the system may also be implemented using a JAVASCRIPT® run-time environment configured to execute JAVASCRIPT® code outside of a web browser. For example, the software elements of the system may also be implemented using NODE.JS® components. NODE.JS® programs may implement several modules to handle various core functionalities. For example, a package management module, such as NPM®, may be implemented as an open source library to aid in organizing the installation and management of third-party NODE.JS® programs. NODE.JS® programs may also implement a process manager, such as, for example, Parallel Multithreaded Machine ("PM2"); a resource and performance monitoring tool, such as, for example, Node Application Metrics ("appmetrics"); a library module for building user interfaces, and/or any other suitable and/or desired module.

The computers discussed herein may provide a suitable website or other internet-based graphical user interface which is accessible by users. In one embodiment, MICROSOFT® company's Internet Information Services (IIS), Transaction Server (MTS) service, and an SQL SERVER® database, are used in conjunction with MICROSOFT® operating systems, WINDOWS NT® web server software, SQL SERVER® database, and MICROSOFT® Commerce Server. Additionally, components such as ACCESS® software, SQL SERVER® database, ORACLE® software, SYBASE® software, INFORMIX® software, MYSQL® software, INTERBASE® software, etc., may be used to provide an Active Data Object (ADO) compliant database management system. In one embodiment, the APACHE® web server is used in conjunction with a LINUX® operating system, a MYSQL® database, and PERL®, PHP, Ruby, and/or PYTHON® programming languages.

For the sake of brevity, data networking, application development, and other functional aspects of the systems (and components of the individual operating components of the systems) may not be described in detail herein. Furthermore, the connecting lines shown in the various figures contained herein are intended to represent exemplary functional relationships and/or physical couplings between the various elements. It should be noted that many alternative or additional functional relationships or physical connections may be present in a practical system.

In various embodiments, the methods described herein are implemented using the various particular machines described herein. The methods described herein may be implemented using the below particular machines, and those hereinafter developed, in any suitable combination, as would be appreciated immediately by one skilled in the art. Further, as is unambiguous from this disclosure, the methods described herein may result in various transformations of certain articles.

In various embodiments, the system and various components may integrate with one or more smart digital assistant technologies. For example, exemplary smart digital assistant technologies may include the ALEXA® system developed by the AMAZON® company, the GOOGLE HOME® system developed by Alphabet, Inc., the HOMEPOD® system of the APPLE® company, and/or similar digital assistant technologies. The ALEXA® system, GOOGLE HOME® system, and HOMEPOD® system, may each provide cloud-based voice activation services that can assist with tasks, entertainment, general information, and more. All the ALEXA® devices, such as the AMAZON ECHO®, AMAZON ECHO DOT®, AMAZON TAP®, and AMAZON FIRE® TV, have access to the ALEXA® system. The ALEXA® system, GOOGLE HOME® system, and HOMEPOD® system may receive voice commands via its voice activation technology, activate other functions, control smart devices, and/or gather information. For example, the smart digital assistant technologies may be used to interact with music, emails, texts, phone calls, question answering, home improvement information, smart home communication/activation, games, shopping, making to-do lists, setting alarms, streaming podcasts, playing audiobooks, and providing weather, traffic, and other real time information, such as news. The ALEXA®, GOOGLE HOME®, and HOMEPOD® systems may also allow the user to access information about eligible transaction accounts linked to an online account across all digital assistant-enabled devices.

The various system components discussed herein may include one or more of the following: a host server or other computing systems including a processor for processing digital data; a memory coupled to the processor for storing digital data; an input digitizer coupled to the processor for inputting digital data; an application program stored in the memory and accessible by the processor for directing processing of digital data by the processor; a display device coupled to the processor and memory for displaying information derived from digital data processed by the processor; and a plurality of databases. Various databases used herein may include: client data; merchant data; financial institution data; and/or like data useful in the operation of the system. As those skilled in the art will appreciate, user computer may include an operating system (e.g., WINDOWS®, UNIX®, LINUX®, SOLARIS®, MACOS®, etc.) as well as various support software and drivers typically associated with computers.

The present system or any part(s) or function(s) thereof may be implemented using hardware, software, or a combination thereof and may be implemented in one or more computer systems or other processing systems. However, the manipulations performed by embodiments may be referred to in terms, such as matching or selecting, which are commonly associated with mental operations performed by a human operator. No such capability of a human operator is necessary, or desirable, in most cases, in any of the operations described herein. Rather, the operations may be machine operations or any of the operations may be conducted or enhanced by artificial intelligence (AI) or machine learning. AI may refer generally to the study of agents (e.g., machines, computer-based systems, etc.) that perceive the world around them, form plans, and make decisions to achieve their goals. Foundations of AI include mathematics, logic, philosophy, probability, linguistics, neuroscience, and decision theory. Many fields fall under the umbrella of AI, such as computer vision, robotics, machine learning, and natural language processing. Useful machines for performing the various embodiments include general purpose digital computers or similar devices. The AI or ML may store data in a decision tree in a novel way.

In various embodiments, the embodiments are directed toward one or more computer systems capable of carrying out the functionalities described herein. The computer system includes one or more processors. The processor is connected to a communication infrastructure (e.g., a communications bus, cross over bar, network, etc.). Various software embodiments are described in terms of this exemplary computer system. After reading this description, it will become apparent to a person skilled in the relevant art(s) how to implement various embodiments using other computer systems and/or architectures. The computer system can include a display interface that forwards graphics, text, and other data from the communication infrastructure (or from a frame buffer not shown) for display on a display unit.

The computer systems also includes a main memory, such as random-access memory (RAM), and may also include a secondary memory. The secondary memory may include, for example, a hard disk drive, a solid-state drive, and/or a removable storage drive. The removable storage drive reads from and/or writes to a removable storage unit. As will be appreciated, the removable storage unit includes a computer usable storage medium having stored therein computer software and/or data.

In various embodiments, secondary memory may include other similar devices for allowing computer programs or other instructions to be loaded into a computer system. Such devices may include, for example, a removable storage unit and an interface. Examples of such may include a program cartridge and cartridge interface (such as that found in video game devices), a removable memory chip (such as an erasable programmable read only memory (EPROM), programmable read only memory (PROM)) and associated socket, or other removable storage units and interfaces, which allow software and data to be transferred from the removable storage unit to a computer system.

The terms "computer program medium," "computer usable medium," and "computer readable medium" are used to generally refer to media such as removable storage drive and a hard disk installed in hard disk drive. These computer program products provide software to a computer system.

The computer system may also include a communications interface. A communications interface allows software and data to be transferred between the computer system and external devices. Examples of such a communications interface may include a modem, a network interface (such as an Ethernet card), a communications port, etc. Software and data transferred via the communications interface are in the form of signals which may be electronic, electromagnetic, optical, or other signals capable of being received by communications interface. These signals are provided to communications interface via a communications path (e.g., channel). This channel carries signals and may be implemented using wire, cable, fiber optics, a telephone line, a cellular link, a radio frequency (RF) link, wireless and other communications channels.

A web client includes any device or software which communicates via any network, such as, for example any device or software discussed herein. The web client may include internet browsing software installed within a computing unit or system to conduct online transactions and/or communications. These computing units or systems may take the form of a computer or set of computers, although other types of computing units or systems may be used, including personal computers, laptops, notebooks, tablets, smart phones, cellular phones, personal digital assistants, servers, pooled servers, mainframe computers, distributed computing clusters, kiosks, terminals, point of sale (POS) devices or terminals, televisions, or any other device capable of receiving data over a network. The web client may include an operating system (e.g., WINDOWS®, WINDOWS MOBILE® operating systems, UNIX® operating system, LINUX® operating systems, APPLE® OS® operating systems, etc.) as well as various support software and drivers typically associated with computers. The web-client may also run MICROSOFT® INTERNET EXPLORER® software, MOZILLA® FIREFOX® software, GOOGLE CHROME™ software, APPLE® SAFARI® software, or any other of the myriad software packages available for browsing the internet.

As those skilled in the art will appreciate, the web client may or may not be in direct contact with the server (e.g., application server, web server, etc., as discussed herein). For example, the web client may access the services of the server through another server and/or hardware component, which may have a direct or indirect connection to an internet server. For example, the web client may communicate with the server via a load balancer. In various embodiments, web client access is through a network or the internet through a commercially-available web-browser software package. In that regard, the web client may be in a home or business environment with access to the network or the internet. The web client may implement security protocols such as Secure Sockets Layer (SSL) and Transport Layer Security (TLS). A web client may implement several application layer protocols including HTTP, HTTPS, FTP, and SFTP.

The various system components may be independently, separately, or collectively suitably coupled to the network via data links which includes, for example, a connection to an Internet Service Provider (ISP) over the local loop as is typically used in connection with standard modem communication, cable modem, DISH NETWORK®, ISDN, Digital Subscriber Line (DSL), or various wireless communication methods. It is noted that the network may be implemented as other types of networks, such as an interactive television (ITV) network. Moreover, the system contemplates the use, sale, or distribution of any goods, services, or information over any network having similar functionality described herein.

The system contemplates uses in association with web services, utility computing, pervasive and individualized computing, security and identity solutions, autonomic computing, cloud computing, commodity computing, mobility and wireless solutions, open source, biometrics, grid computing, and/or mesh computing.

Any of the communications, inputs, storage, databases or displays discussed herein may be facilitated through a website having web pages. The term "web page" as it is used herein is not meant to limit the type of documents and applications that might be used to interact with the user. For example, a typical website might include, in addition to standard HTML documents, various forms, JAVA® applets, JAVASCRIPT® programs, active server pages (ASP), common gateway interface scripts (CGI), extensible markup language (XML), dynamic HTML, cascading style sheets (CSS), AJAX (Asynchronous JAVASCRIPT And XML) programs, helper applications, plug-ins, and the like. A server may include a web service that receives a request from a web server, the request including a URL and an IP address (192.168.1.1). The web server retrieves the appropriate web pages and sends the data or applications for the web pages to the IP address. Web services are applications that are capable of interacting with other applications over a communications means, such as the internet. Web services are typically based on standards or protocols such as XML, SOAP, AJAX, WSDL and UDDI. For example, representational state transfer (REST), or RESTful, web services may provide one way of enabling interoperability between applications.

The computing unit of the web client may be further equipped with an internet browser connected to the internet or an intranet using standard dial-up, cable, DSL, or any other internet protocol. Transactions originating at a web client may pass through a firewall in order to prevent unauthorized access from users of other networks. Further, additional firewalls may be deployed between the varying components of CMS to further enhance security.

Benefits, other advantages, and solutions to problems have been described herein regarding specific embodiments. Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Different cross-hatching is used throughout the figures to denote different parts but not necessarily to denote the same or different materials.

Systems, methods, and apparatus are provided herein. In the detailed description herein, references to "one embodiment," "an embodiment," "various embodiments," etc., indicate that the embodiment described may include a particular feature, structure, or characteristic, but every embodiment may not necessarily include the feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element herein is to be construed under the provisions of 35 U.S.C. 212(f) unless the element is expressly recited using the phrase "means for." As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

Finally, any of the above-described concepts can be used alone or in combination with any or all the other above-described concepts. Although various embodiments have been disclosed and described, one of ordinary skill in this art would recognize that certain modifications would come within the scope of this disclosure. Accordingly, the description is not intended to be exhaustive or to limit the principles described or illustrated herein to any precise form. Many modifications and variations are possible considering the above teaching.

What is claimed is:

1. A portable medical device, comprising:
   a main body extending from a first end to a second end;
   a first camera disposed at the first end, the first camera comprising an otoscopic lens and configured to facilitate examination of an ear of a patient, the otoscopic lens having a fixed magnification; and
   a second camera disposed at the second end, the second camera comprising a video scope configured for adjustable magnification of an object, the second camera configured to facilitate examination of a throat of the patient.

2. The portable medical device of claim 1, wherein:
   the main body defines a longitudinal axis,
   the first camera defines a first optical axis,
   the second camera defines a second optical axis, and
   the first optical axis and the second optical axis are substantially parallel to the longitudinal axis.

3. The portable medical device of claim 2, wherein the first optical axis and the second optical axis are co-axial.

4. The portable medical device of claim 1, wherein the main body defines a grip.

5. The portable medical device of claim 1, further comprising a first button electrically coupled to the first camera, the first button configured to freeze a first frame of the first camera.

6. The portable medical device of claim 5, further comprising a second button electrically coupled to the second camera, the second button configured to freeze a second frame of the second camera.

7. The portable medical device of claim 1, further comprising a plurality of lights disposed circumferentially around the first camera.

8. A portable medical kit comprising the portable medical device of claim 1, the portable medical kit further comprising a detachable component, the detachable component comprising:
   an attachment feature configured to couple to the main body,
   a mount that extends outward from the attachment feature, and
   an elongated member extending axially from the mount.

9. The portable medical device of claim 1, further comprising an extended mirror coupled to the main body.

10. The portable medical device of claim 1, wherein the video scope of the second camera comprises a near-far general video scope.

11. An electronic system for a portable medical device, comprising:
    a transistor circuit comprising a first power rail and a second power rail, the transistor circuit configured to determine a body temperature of a user;
    a first image sensor;
    a second image sensor;
    an infrared sensor that is disposed proximal the second image sensor and distal to the first image sensor;
    a transmitter;
    a controller in electronic communication with the first image sensor, the second image sensor, the infrared sensor, and the transmitter, the controller configured to command the transmitter to transmit data to a user device; and
    a shared frame buffer and pass through disposed electrically between the controller and the first image sensor and between the controller and the second image sensor.

12. The electronic system of claim 11, wherein the controller is configured to transmit a first video data from the first image sensor and a second video data from the second image sensor.

13. The electronic system of claim 11, further comprising a WiFi module, wherein the WiFi module is configured to transmit the data to the user device through a network.

14. A portable medical kit, comprising:
    a portable medical device including a main body, a first camera, a second camera, and a first control button, the main body extending from a first end to a second end, the first camera disposed at the first end, the second camera disposed at the second end, the first control button configured to control a parameter of the first camera, the first camera comprising an otoscopic lens and configured to facilitate examination of an ear of the patient, the second camera comprising a video scope and configured to facilitate examination of a throat of a patient;
    an extended mirror configured to detachably couple to the main body; and
    a detachable component configured to detachably couple to the main body.

15. The portable medical kit of claim 14, wherein the first camera defines a first optical axis and the main body defines a longitudinal axis, and wherein the first optical axis and the longitudinal axis are substantially parallel.

16. The portable medical kit of claim 14, wherein the portable medical device further comprises a plurality of lights at the second end of the main body.

17. The portable medical kit of claim 16, wherein the plurality of lights are configured to illuminate the object within a field of view of the second camera.

18. The portable medical kit of claim 14, wherein the detachable component comprises:
    an attachment feature configured to couple to the main body,
    a mount that extends outward from the attachment feature, and
    an elongated member extending axially from the mount.

* * * * *